(12) United States Patent
Batiste

(10) Patent No.: US 7,108,673 B1
(45) Date of Patent: Sep. 19, 2006

(54) A-V DIALYSIS GRAFT CONSTRUCTION

(76) Inventor: Stan Batiste, 808 Sir James Bridge Way, Las Vegas, NV (US) 89145

( * ) Notice: Subject to any disclaimer, the term of this patent is extended or adjusted under 35 U.S.C. 154(b) by 450 days.

(21) Appl. No.: 10/614,450

(22) Filed: Jul. 7, 2003

(51) Int. Cl.
- *A61M 37/00* (2006.01)
- *A61M 25/00* (2006.01)
- *A61M 5/00* (2006.01)
- *A61F 2/06* (2006.01)

(52) U.S. Cl. .............. 604/6.16; 604/5.01; 604/264; 623/1.13

(58) Field of Classification Search ............ 604/7–10, 604/4.01, 5.01–5.04, 6.16, 19, 27, 28, 43, 604/264, 523, 508–9; 623/1.1, 1.13, 1.25, 623/1.36, 1.3, 1.31, 1.49, 11.11, 23.64, 23.7, 623/23.71, 23.75, 23.76
See application file for complete search history.

(56) References Cited

U.S. PATENT DOCUMENTS

| | | | |
|---|---|---|---|
| 3,826,257 A * | 7/1974 | Buselmeier | 604/8 |
| 4,549,879 A | 10/1985 | Groshong et al. | 604/247 |
| 4,753,640 A | 6/1988 | Nichols et al. | 604/247 |
| 5,713,859 A | 2/1998 | Finch, Jr. et al. | 604/93 |
| 5,800,514 A * | 9/1998 | Nunez et al. | 623/1.51 |
| 5,849,036 A * | 12/1998 | Zarate | 623/1.31 |
| 6,146,414 A * | 11/2000 | Gelman | 623/1.23 |
| 6,338,724 B1 * | 1/2002 | Dossa | 604/8 |
| 6,371,981 B1 * | 4/2002 | Yang et al. | 623/1.13 |
| 6,461,321 B1 | 10/2002 | Quinn | 604/43 |
| 6,585,762 B1 * | 7/2003 | Stanish | 623/1.3 |
| 6,598,278 B1 * | 7/2003 | Chen et al. | 29/235 |

* cited by examiner

*Primary Examiner*—Patricia Bianco
(74) *Attorney, Agent, or Firm*—Sturm & Fix LLP

(57) ABSTRACT

An improvement to an A–V dialysis graft construction (10) that includes an elongated length of polymer tubing (12) having an inlet end (13) and an outlet end (14) for attachment to access needles (15) (15) wherein, the improvement includes a normally reduced diameter intermediate portion (16) that restricts the flow of blood from the inlet end (13) of the length of polymer tubing (12) to the outlet end (14) for the purpose of minimizing venous stenosis.

2 Claims, 3 Drawing Sheets

A-V DIALYSIS GRAFT CONSTRUCTION

CROSS REFERENCE TO RELATED APPLICATIONS

Not applicable.

BACKGROUND OF THE INVENTION

1. Field of the Invention

The present invention relates to the field of hemo-dialysis apparatus in general and in particular to an arterial-venous graft having an intra-graft stenosis formed integrally therein.

2. Description of Related Art

As can be seen by reference to the following U.S. Pat. Nos. 6,461,321 B1; 6,146,414; 5,713,859; 4,753,640; and, 4,549,879, the prior art is replete with myriad and diverse graft constructions employed for hemo-dialysis procedures.

While all of the aforementioned prior art constructions are more than adequate for the basic purpose and function for which they have been specifically designed, they are uniformly deficient with respect to their failure to provide a simple, efficient, and practical means of forming an artificial intra-graft stenosis to provide increased blood flow resistance during those periods when the higher blood flow rates required by hemo-dialysis are not present.

As virtually all physicians and health care specialists are aware, the process of hemo-dialysis requires large volumes of blood to be circulated through a filtration device. However, with prior art, A–V designs having a uniform bore configurations the continued high pressure blood flow into veins creates venous irritation and scarring leading to "stenosis" and eventual occlusion as well as causing increased cardiac demands.

As a consequence of the foregoing situation, there has existed a longstanding need among medical personnel for a new and improved A–V stent graft construction having a reduced diameter portion, and the provision of such a construction is the stated objective of the present invention.

BRIEF SUMMARY OF THE INVENTION

Briefly stated, the improved A–V graft construction that forms the basis of the present invention comprises an elongated flexible tubular member having a generally uniform inside diameter with the notable exception of a reduced diameter intermediate portion which forms the crux of the present invention.

As will be explained in greater detail further on in the specification, in the first version of the preferred embodiment, the reduced diameter intermediate portion comprises a gently tapered segment having gradually diminishing and gradually expanding sections, and, in the second version of the preferred embodiment, the reduced diameter intermediate portion comprises an abruptly constricted section.

In addition, in both versions of the preferred embodiment, the average overall inside diameter of the generally uniform diameter tubular member is between ½ to greater than the average inside diameter of the reduced diameter ⅕ intermediate portion.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figures 2, 2A, 2B, 2C:
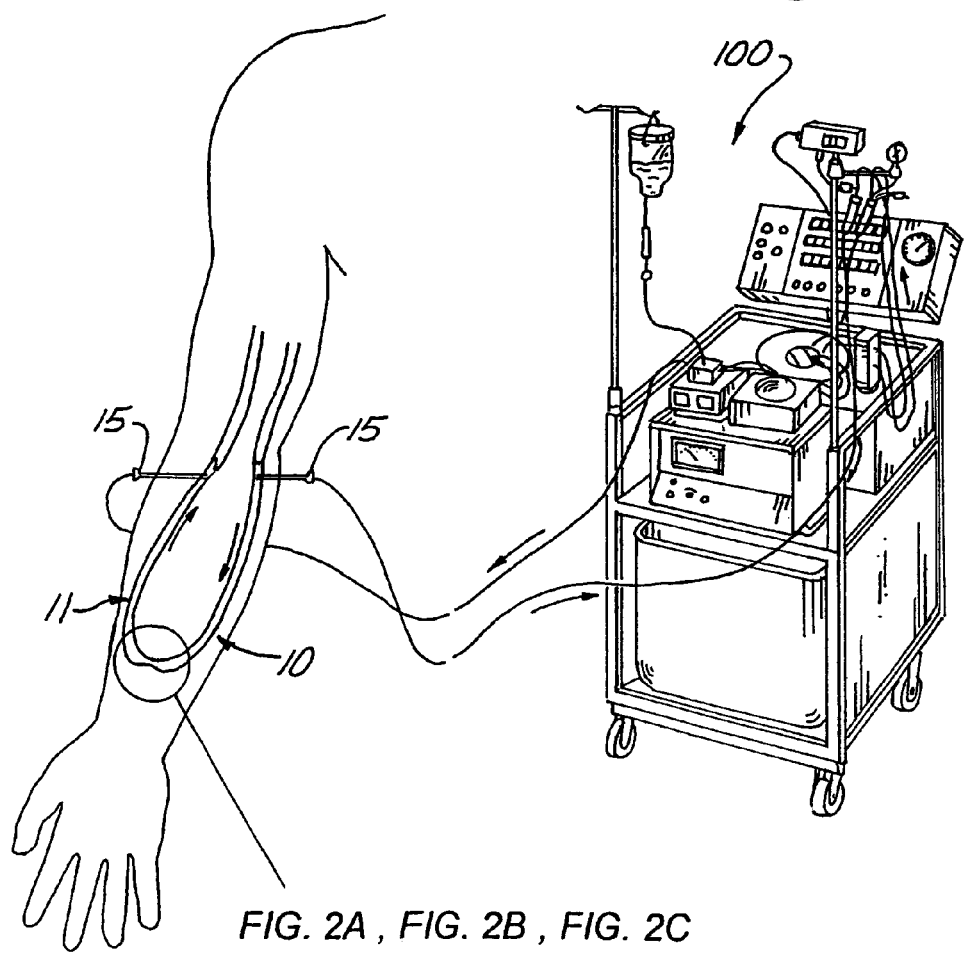
FIG. 2 is a representative perspective view of the A–V graft construction that forms the basis of the present invention.
FIG. 2A is an enlarged detail view of the smoothly constricted version of the invention.
FIG. 2B is an enlarged detail view of the abruptly constricted version of the invention; and, FIG. 2C is an enlarged detail view of a hybrid version of the invention.
Figure 2A:
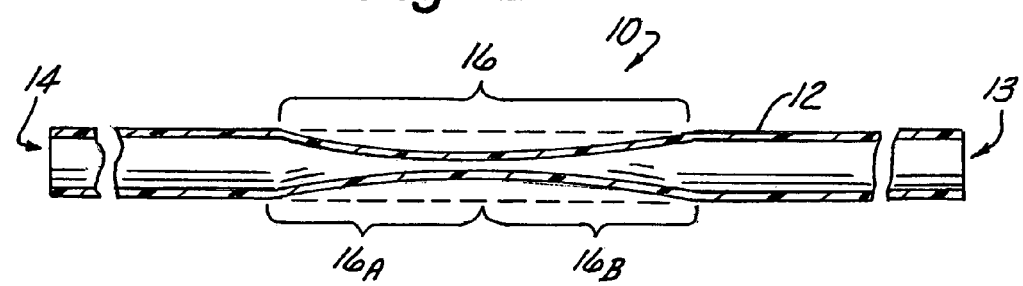
Figure 2B:
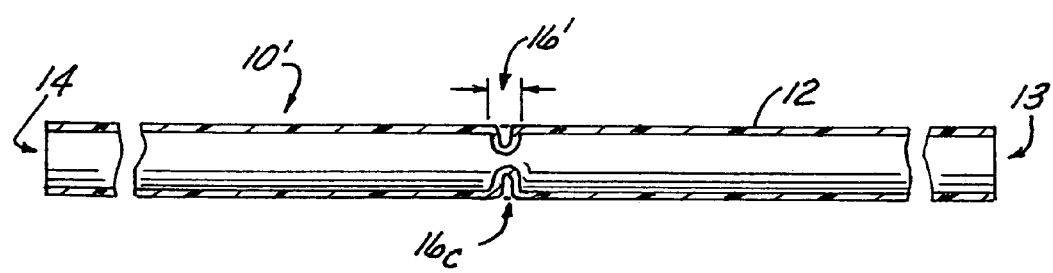
Figure 2C:

As can be seen by reference to the drawings, and in particular to FIG. 2, the improved A–V graft construction that forms the basis of the present invention is designated generally by the reference number 10. Prior to embarking on a detailed description of the improved graft construction 10, it would first be advisable to describe the conventional graft construction 1 currently used as standard equipment in virtually all modern hemo-dialysis procedures.

Figure 1:
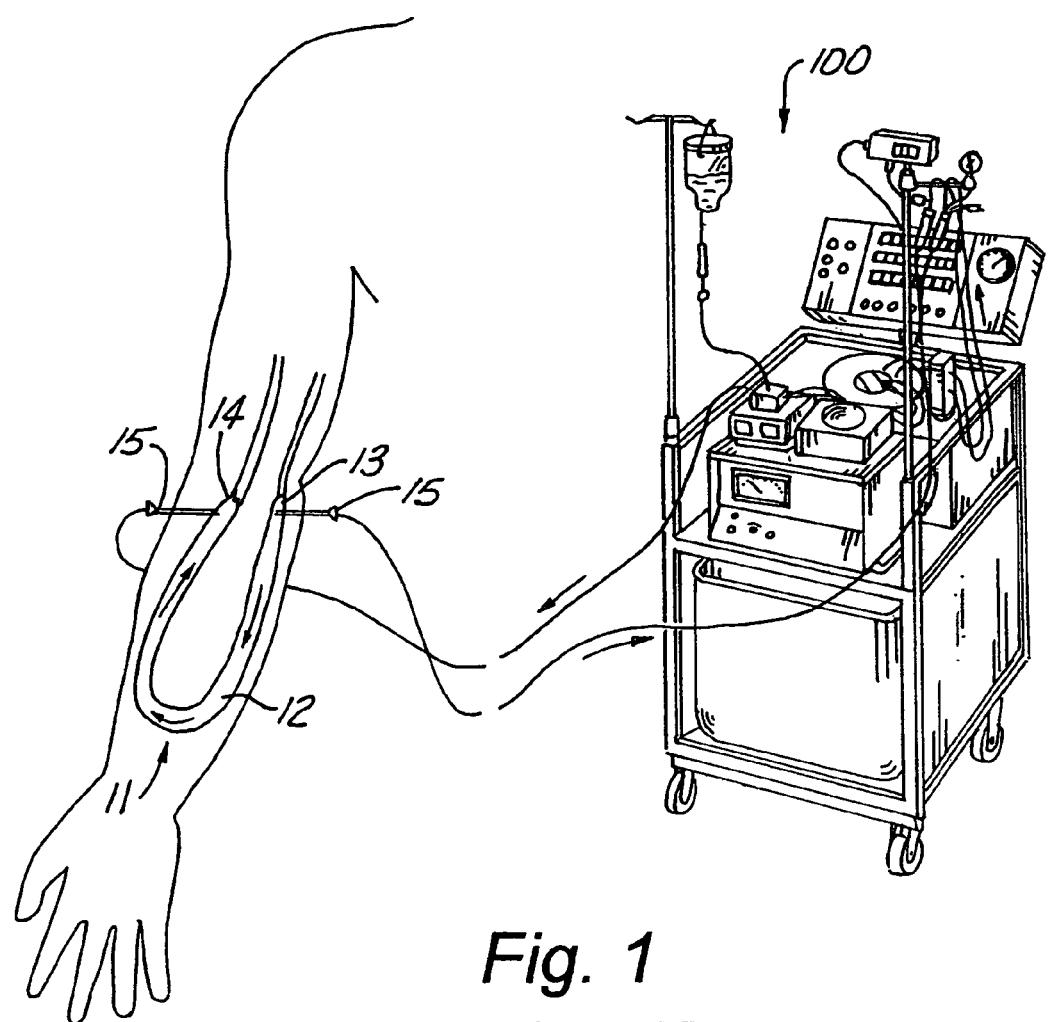
FIG. 1 is a perspective view of the prior art uniform inside diameter A–V graft construction currently employed in hemo-dialysis procedures.

As shown in FIG. 1, the prior art graft construction 11 includes an elongated length of hollow polymer tubing 12 having a uniform inside diameter extending from the inlet end 13 to the outlet end 14 wherein, the inlet end 13 defines the arterial anastomosis.

In addition, the conventional graft construction 11, as well as, the improved graft construction 10 are commonly surgically placed within a patient's upper arm or forearm and connected via access needles 15 15 to a hemo-dialysis machine that withdraws blood from the arterial end 13 and removes impurities from the blood prior to re-introducing the cleansed blood through the venous end 14.

As was mentioned previously, the hemo-dialysis procedure requiring abnormally high blood flow rates through the conventional uniform internal diameter graft constructions 11 and the presence of the conventional graft construction 11 allows the elevated blood flow rates to continue un-subsided during those periods when the access needles 15 15 are not connected to the hemo-dialysis machine 100.

As a direct consequence of these elevated blood flow rates, increased cardiac demands are imposed on the heart as blood is bypassed past the distal circulation and the high pressure flow rates results in venous irritation leading to stenosis and occlusion which typically occurs at the venous anastomosis.

As a consequence of the foregoing situation, and as shown in FIG. 2, the improved graft construction 10 of the present invention includes an elongated length of polymer tubing 12 having an inlet end 13, and outlet end 14, and a reduced diameter intermediate portion 16 which forms the heart of this invention.

In the first version of the preferred embodiment depicted in FIG. 2A, the intermediate portion 16 includes a gradually diminishing segment 16A and a gradually expanding segment 16B wherein, the minimum inside diameter of the intermediate portion 16 is equal to or less than ⅔ rds of the generally uniform inside diameter of the remainder of the length of polymer tubing 12.

As can further be appreciated by reference to FIG. 2B in the second version of the preferred embodiment, the improved graft construction 10' has a relatively abrupt reduced diameter intermediate portion 16' created by a crimped segment 16C in the length of polymer tubing 12.

Furthermore, as depicted in FIG. 2C, this invention also contemplates a hybrid version including an abruptly crimped segment 16C' that is selectively disposed upstream or downstream of a gradually expanding or diminishing segment 16A/B.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. An improved A–V dialysis graft construction that includes an elongated length of polymer tubing having an inlet end, an outlet end, and a generally uniform inside diameter over a substantial portion of the length of polymer tubing wherein, the improvement comprises:
    a reduced diameter intermediate portion formed between said inlet end and said outlet end; wherein, the reduced diameter intermediate portion comprises an abrupt crimped segment.

2. The improvement as in claim 1, wherein, the reduced diameter intermediate portion further comprises a gradually expanding segment.

* * * * *